(12) United States Patent
Podsiadlo et al.

(10) Patent No.: US 11,331,658 B2
(45) Date of Patent: May 17, 2022

(54) TRANSALKYLATION START-UP PROCESSES FOR SUPPORTED PRECIOUS METAL CATALYST

(71) Applicant: ExxonMobil Chemical Patents Inc., Baytown, TX (US)

(72) Inventors: Paul Podsiadlo, Humble, TX (US); Robert G. Tinger, Friendswood, TX (US); Todd E. Detjen, Bellaire, TX (US); Jesus A. Ramos, Houston, TX (US); Jeffrey L. Andrews, Houston, TX (US); Travis D. Sparks, Deer Park, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 131 days.

(21) Appl. No.: 16/816,762

(22) Filed: Mar. 12, 2020

(65) Prior Publication Data
US 2020/0306744 A1  Oct. 1, 2020

Related U.S. Application Data

(60) Provisional application No. 62/824,425, filed on Mar. 27, 2019.

(51) Int. Cl.
*B01J 37/18* (2006.01)
*B01J 37/02* (2006.01)
(Continued)

(52) U.S. Cl.
CPC .............. *B01J 37/18* (2013.01); *B01J 6/001* (2013.01); *B01J 37/0201* (2013.01);
(Continued)

(58) Field of Classification Search
CPC ........ B01J 6/001; B01J 29/061; B01J 29/068; B01J 37/0201; B01J 37/0236; B01J 37/08;
(Continued)

(56) References Cited

U.S. PATENT DOCUMENTS 9,868,117 B2   1/2018  Detjen et al.
10,583,425 B2  3/2020  McCarthy et al.
(Continued)

FOREIGN PATENT DOCUMENTS

WO   2015/167667 A   11/2015
WO   2016/064590 A   4/2016

*Primary Examiner* — Brian A McCaig

(57) ABSTRACT

Processes for activating precious metal-containing catalysts. The processes can decrease the amount of high purity hydrogen required for starting up a catalytic conversion process such as transalkylation of heavy aromatics, without detrimental impact to the metal activity. The processes can include a low temperature treatment step with a high purity first gas, such as hydrogen generated by electrolysis and/or reformer hydrogen diluted with high purity inert gas, and a high temperature treatment step with a low purity second gas such as the reformer hydrogen. Also, the processes can include mixing a hydrogen gas of high or low purity with a high purity inert gas to form a gas mixture with a proportion of hydrogen no less than 2% and a reduced carbon monoxide concentration relative to the low purity hydrogen, and contacting the catalyst with the gas mixture.

24 Claims, 3 Drawing Sheets

(51) Int. Cl.
*B01J 6/00* (2006.01)
*C07C 15/08* (2006.01)
*C07C 5/22* (2006.01)
*B01J 37/08* (2006.01)
*C01B 3/06* (2006.01)

(52) U.S. Cl.
CPC .......... *B01J 37/0236* (2013.01); *B01J 37/08* (2013.01); *C07C 5/222* (2013.01); *C07C 15/08* (2013.01); *C01B 3/06* (2013.01); *C01B 2203/0238* (2013.01); *C01B 2203/047* (2013.01)

(58) Field of Classification Search
CPC .......... B01J 37/18; C07C 5/222; C07C 15/08; C01B 3/06; C01B 3/34; C01B 2203/0238; C01B 2203/047
See application file for complete search history.

(56) References Cited

U.S. PATENT DOCUMENTS

| | | | |
|---|---|---|---|
| 2009/0264686 A1* | 10/2009 | Holladay | B01J 23/8896 568/861 |
| 2018/0318812 A1 | 11/2018 | Bedard et al. | |
| 2019/0031575 A1* | 1/2019 | Pan | B01J 23/8892 |

* cited by examiner

TRANSALKYLATION START-UP PROCESSES FOR SUPPORTED PRECIOUS METAL CATALYST

CROSS-REFERENCE TO RELATED APPLICATIONS

This application claims priority to U.S. Ser. No. 62/824,425, filed Mar. 27, 2019, herein incorporated by reference.

FIELD

This disclosure relates to aromatic hydrocarbon conversion processes and activation processes for precious-metal-containing catalysts. In particular, this disclosure relates to activation processes using hydrogen for precious-metal-containing aromatic hydrocarbon conversion catalysts, and to aromatic hydrocarbon conversion processes using such activated catalysts.

BACKGROUND

Catalysts comprising a precious metal, such as those used in aromatic hydrocarbon conversion processes (e.g., transalkylation, dealkylation, and the like), are routinely activated before normal use thereof by using hydrogen to reduce the precious metal in oxidized state (e.g., $PtO_2$) to elemental state (e.g., Pt). The activation can be advantageously performed in the reactor (i.e., in situ) before the normal operation of the intended aromatic hydrocarbon conversion reaction starts. Catalysts containing precious metal, especially those containing low levels of precious metal or highly dispersed precious metal, can be impacted during in-plant activation by low levels of carbon monoxide that may be present in reformer or other plant sources of hydrogen gas. While the mechanism is not fully understood, it is believed a small amount of CO can bind irreversibly to Pt during the conversion process, most likely resulting in a weakened interaction with metal support, which then leads to metal migration, agglomeration, and sintering. Agglomeration and sintering decrease dispersion and activity of the precious metal in the catalyst composition because of decreased surface area of the active metal sites.

In aromatic hydrocarbon transalkylation technology, aromatic hydrocarbon isomerization technology, and other aromatic hydrocarbon conversion processes, some new generations of catalysts have very low precious metal content, thus making them more sensitive to metal sintering associated with the presence of CO in hydrogen used for in-situ reduction. This can result in negative impact on the performance of the precious metal, poor saturation of ethylene and other olefins, and high ethylbenzene and ethylated C9+ product yields, which can be highly undesirable. In cases where ex-situ reduction or activation is not possible, a successful in-situ activation may thus require high purity hydrogen with exceedingly low CO concentration, e.g., electrolytic hydrogen, which is very expensive and sometimes not available at all.

From the cost perspective, it would be preferred to use available plant sources of hydrogen, e.g., refinery hydrogen sourced from a reformer unit, which can contain up to 10 vppm by volume CO. Unfortunately, we have found that a 10 vppm by volume CO concentration can result in significant precious metal activity debit, especially for those catalysts comprising precious metal at a low level. High purity hydrogen, ideally with no greater than 0.1 vppm by volume CO, is therefore recommended for the reduction/activation step of the precious metal catalyst. While high purity hydrogen can be produced by electrolysis, e.g., using a portable electrolytic hydrogen truck, it can be costly and does not necessarily meet the desired CO content of no greater than 0.1 vppm by volume.

What is needed is a catalyst activation technology that can inhibit precious metal sintering without the requirement of a large volume of high purity hydrogen that is presently required. Such technology could result in a significant cost saving for start-up of an aromatic hydrocarbon conversion process using such catalysts, especially such catalysts comprising precious metals at a low concentration.

SUMMARY

It has been found, in a surprising manner, that catalysts comprising precious metal at a low concentration for converting hydrocarbons, such as transalkylation catalysts, can be activated first ex-situ or in-situ using a hydrogen-containing gas comprising CO at a low concentration and optionally a diluent inert gas, followed by an in-situ or ex-situ activation using a hydrogen-containing gas comprising CO at an elevated level (e.g., reformer hydrogen), to a high-activity catalyst. This is highly advantageous compared to an in-situ activation process using high-purity electrolysis hydrogen only. This is also in contrast to an activation process using hydrogen-containing gas containing CO at an elevated level such as reformer hydrogen only, which can yield a catalyst with lower activity.

Thus, a first aspect of this disclosure relates to a process for activating a catalyst composition comprising a precious metal, the process comprising: (I) providing the catalyst composition comprising the precious metal, wherein the concentration of the precious metal in the catalyst composition is from 0.01 wt % to 5.0 wt %, expressed as weight percentage of the precious metal based on the total weight of the catalyst composition; (II) contacting the catalyst composition with a first gas at a first temperature in a range from 150° C. to 300° C., the first gas comprising hydrogen and no more than 1 vppm carbon monoxide, based on the total volume of the first gas; and (III) after step (II), contacting the catalyst composition with a second gas comprising hydrogen at a second temperature not lower than 340° C., wherein the second gas further comprises carbon monoxide at a concentration of no less than 1 vppm, based on the total volume of the second gas.

A second aspect of this disclosure relates to process for activating a catalyst composition, the process comprising the following steps in the following order: (i) providing a catalyst composition comprising a precious metal at a concentration from 0.01 wt % to 5.0 wt %, based on the total weight of the catalyst composition; (ii) disposing the catalyst composition in a reactor; (iii) purging the catalyst composition and the reactor with an inert gas; (iv) purging the catalyst composition and the reactor with a first gas comprising carbon monoxide at a concentration no greater than 0.5 vppm; (v) heating the catalyst composition from an ambient temperature to a first temperature in a range from 150° C. to 300° C.; (vi) maintaining the catalyst composition in proximity to the first temperature for a period from 1 hour to 24 hours in the presence of the first gas; (vii) heating the catalyst composition from the first temperature to a second temperature no less than 340° C.; and (viii) maintaining the catalyst composition in proximity to the second activation temperature for a period from 0.1 hour to 8 hours in the presence of a second gas comprising carbon monoxide at a concentration no less than 1 vppm.

A third aspect of this disclosure relates to process for activating a catalyst composition comprising a precious metal, the process comprising: (I) providing the catalyst composition comprising the precious metal, wherein the concentration of the precious metal in the catalyst composition is from 0.01 wt % to 5.0 wt %, expressed as weight percentage of the precious metal based on the total weight of the catalyst composition; (II) mixing a high purity inert gas comprising no more than 1 vppm carbon monoxide, with a hydrogen gas stream comprising no more than 20 vppm carbon monoxide, to form a gas mixture comprising no less than 2 percent hydrogen by volume; and (III) contacting the catalyst composition with the gas mixture at a temperature no lower than 150° C.

DETAILED DESCRIPTION

Figure 1:
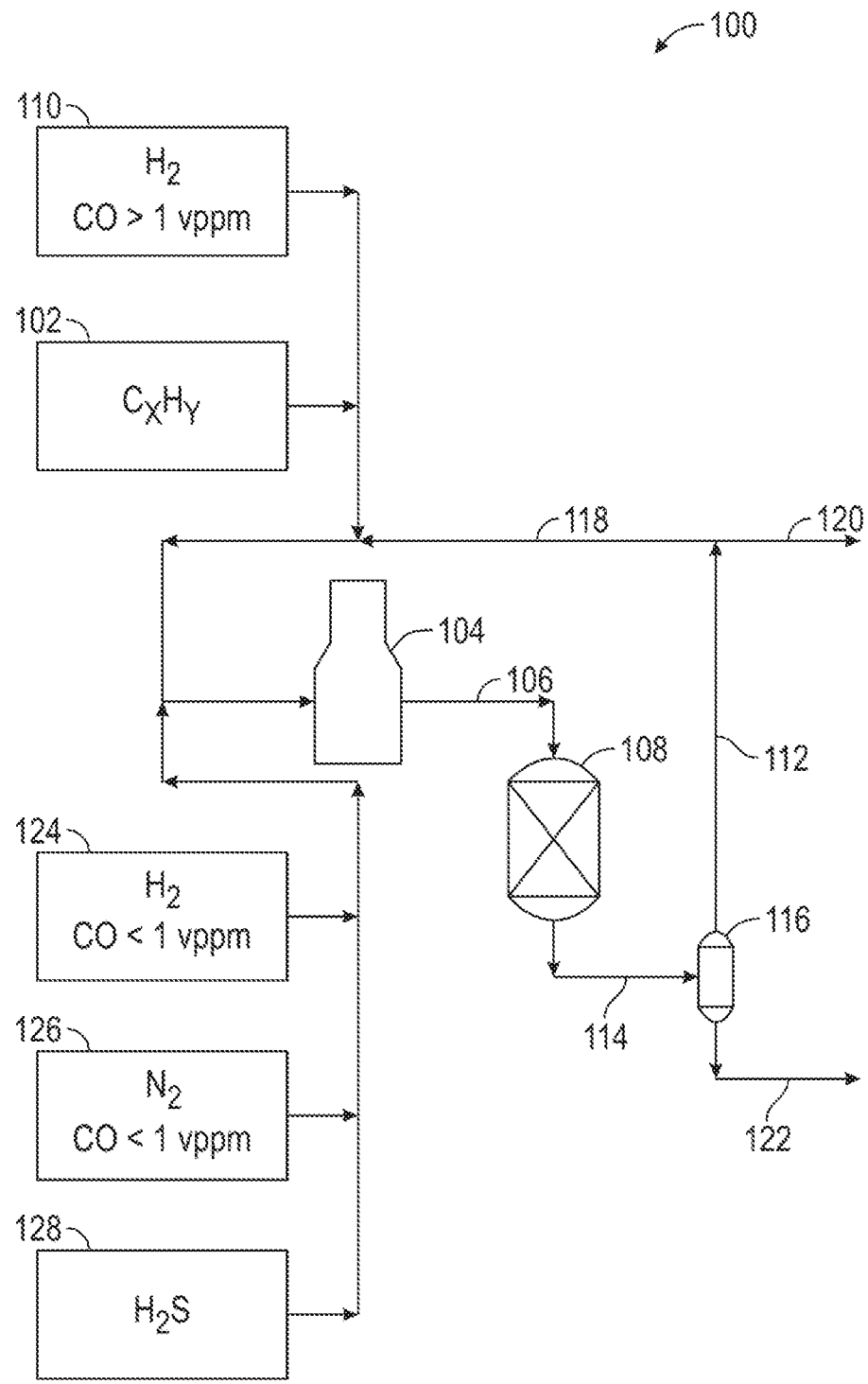
FIG. 1 is a generalized, simplified schematic flow diagram for a transalkylation process according to embodiments of the present invention.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "an ether" include embodiments where one, two or more ethers are used, unless specified to the contrary or the context clearly indicates that only one ether is used.

For the purposes of this disclosure, the nomenclature of elements is pursuant to the version of Periodic Table of Elements as described in CHEMICAL AND ENGINEERING NEWS, 63(5), pg. 27 (1985).

Throughout the entire specification, including the claims, the following terms shall have the indicated meanings.

The term "and/or" refers to both the inclusive "and" case and the exclusive "or" case, and such term is used herein for brevity. For example, a composition comprising "A and/or B" may comprise A alone, B alone, or both A and B.

As used herein, "activation" refers to the process of making a substance chemically or catalytically reactive.

As used herein, the terms "no," "essentially no," "free of," and "essentially free of" with respect to a component of a stream or mixture mean that the component is not present, or if present is present in an amount that is no more than as a typical impurity, or no more than 5 percent by weight, preferably no more than 2 percent by weight.

As used herein, the term "high purity" in relation to gases or gas streams means that the gas or stream contains at least 99.9999 volume percent of the primary gas or gases, including inert gas, and/or no more than 1 vppm CO by volume; and the term "low purity" means that the gas or stream contains more than 1 vppm CO or another transalkylation catalyst deactivating component such as halogens, oxides, and so on.

Weight hourly space velocity (WHSV), as used herein, is the mass flow rate of hydrocarbons in all feed streams to a catalytic reactor per mass of catalyst per hour, e.g., grams hydrocarbon/gram catalyst per hour.

As used herein, "stream" refers to process material flow in one or more pipes or channels or part(s) thereof, whether solid or fluid, including vapor, liquid, slurry, foam, mist, etc. Where a particular component is specified for a separate or isolated stream, it is understood that the stream contains at least 2 percent of that component by total weight of the stream, e.g., a "benzene stream" refers to a stream containing at least 5 percent benzene by total weight of the stream.

As used herein, unless otherwise indicated, in relation to gases "ppm" means parts per million by volume or "vppm", and in relation to liquids or solids, "ppm" means parts per million by weight or "ppmw" unless otherwise stated. Similarly, "percent" in relation to gases means percent by volume and in relation to liquids or solids means percent by weight unless otherwise stated.

In the following discussion, reference to a carbon-containing compound such as a hydrocarbon may be made in the shorthand form of "Cn" where n refers to the number of carbon atoms in the compound regardless of the number of hydrogen or heteroatoms in the compound(s). If a plus or minus sign is used, it designates a range of carbon atoms containing n carbon atoms or more or n carbon atoms or less. For example, "C9+" refers to compounds such as hydrocarbons having 9 or more carbon atoms, and "C7-" refers to compounds such as hydrocarbons having 7 or fewer carbon atoms.

We have observed that after initial low-temperature exposure of a low-concentration precious metal catalyst composition to an activation gas of high purity, e.g., such as electrolytic hydrogen containing less than 1 vppm carbon monoxide, the high purity activation gas can be subsequently replaced with low purity activation gas, e.g., reformer hydrogen containing up to 10 vppm CO, to complete the activation process at a higher temperature, without detrimental impact to precious metal activity in the catalyst composition. This can decrease the amount of high purity hydrogen that would otherwise be required should the whole activation process utilize high-purity hydrogen.

We have also observed that a mixture of hydrogen and an inert gas can be used to activate low-concentration precious metal catalyst compositions, providing that there is sufficient hydrogen to reduce the precious metal in the catalyst. Because these catalyst compositions contain low levels of the precious metal, e.g., less than 5.0 wt %, only a very low level of hydrogen is needed, e.g., 2 or 4 percent hydrogen by volume. On the other hand, the allowable carbon monoxide level in the dilute hydrogen does not appear to be any lower than when using high purity hydrogen, e.g., 1 vppm CO. Thus, where a high purity inert gas is available, it is now possible to use a much lower amount of high purity hydrogen than previously thought to be necessary. Or, the need for high purity hydrogen can be eliminated altogether. For example, a high purity nitrogen stream with less than 0.1 vppm CO can be used to dilute a 10 vppm CO reformer hydrogen stream at 90:10 for all or a part of the activation with a gas mixture of 90 percent nitrogen and 10 percent hydrogen, by volume, with 1 vppm CO.

In embodiments according to the present invention, high purity hydrogen and/or inert gas is unexpectedly required only in the initial activation of low precious metal-containing transalkylation catalysts up to a first relatively low activation temperature, and low purity activation gas can optionally be used at temperatures above the first activation temperature. Moreover, the hydrogen content of the activation gas can be relatively low, e.g., 2 vol % or 4 vol %, thus allowing the use of an inert gas as a diluent to reduce the overall CO content to 1 vppm or less.

In one aspect, the present invention provides a process for activating a catalyst composition comprising a precious metal, the process comprising: (I) providing the catalyst composition comprising the precious metal, wherein the concentration of the precious metal in the catalyst composition is from 0.01 wt % to 5.0 wt %, expressed as weight percentage of the precious metal based on the total weight of the catalyst composition; (II) contacting the catalyst composition with a first gas at a first temperature in a range from 150° C. to 300° C., the first gas comprising hydrogen and no more than 1 vppm carbon monoxide; and (III) after step (II), contacting the catalyst composition with a second gas at a second temperature not lower than 340° C., wherein the second gas comprises hydrogen and carbon monoxide at a concentration no less than 1 vppm.

In any embodiment, the first gas can further comprise an inert gas, preferably nitrogen.

In any embodiment, the second gas can comprise hydrogen and carbon monoxide at a concentration of no less than 3 vppm and no greater than 20 vppm. Preferably the second gas comprises reformer hydrogen produced by a hydrocarbon reforming process and the carbon monoxide concentration is no greater than 10 vppm.

In any embodiment, the first gas can be formed by diluting the reformer hydrogen with high purity inert gas to decrease the carbon monoxide concentration of the resulting first gas relative to the reformer hydrogen. Preferably the inert gas comprises carbon monoxide at a concentration of no more than 0.1 vppm.

In any embodiment, the first gas can comprise at least 2 volume percent hydrogen and no more than 98 volume percent inert gas. Preferably the first gas comprises at least 4 volume percent hydrogen and no more than 96 volume percent inert gas.

The first gas preferably comprises carbon monoxide at a concentration of no greater than 0.5 vppm, more preferably no greater than 0.1 vppm, and often comprises or consists of an electrolytic hydrogen stream formed by electrolytic decomposition of water.

In any embodiment, the catalyst composition can comprise the precious metal at a concentration no greater than 0.1 wt %, based on the total weight of the catalyst composition.

In any embodiment, the process further comprising, after step (I) and before step (II): (Ia) heating the catalyst composition in the presence of the first hydrogen stream from ambient temperature to the first temperature, preferably wherein the ambient temperature is no higher than 50° C.

In any embodiment, the process further comprises, after step (II) and before step (III): (IIa) heating the catalyst composition from the first temperature to the second temperature in the presence of the first gas, the second gas, or a mixture of both.

Often, the heating in respective steps (Ia) and (IIa) comprises heating the catalyst composition at a temperature elevation rate in a range from 0.01° C. per minute to 5° C. per minute. Preferably the temperature elevation rate is no more than 1° C. per minute.

In any embodiment, step (I) comprises: (I-A) after step (I) and before step (II), disposing the catalyst composition in a reactor; (I-B) after step (I-A), purging the catalyst composition and the reactor with inert gas; and (I-C) after step (I-B), purging the catalyst composition and the reactor with the first gas.

In any embodiment, in step (II), the catalyst composition is held in proximity to the first temperature in the presence of the first gas for a period of from 1 hour to 24 hours, preferably from 3 hours to 12 hours.

In any embodiment, in step (III), the catalyst composition is held in proximity to the second temperature in the presence of the second gas for a period of from 0.2 hour to 8 hours, preferably from 0.5 hour to 4 hours.

In any embodiment, the second temperature is no higher than 515° C., preferably no higher than 425° C.

In any embodiment, the first and second gases can have an absolute hydrogen partial pressure in a range from 2 kPa to 5000 kPa, preferably at least 4 kPa.

In any embodiment, step (I) comprises: (I.1) providing a zeolite; (I.2) impregnating the zeolite with a solution of the precious metal to obtain an impregnated zeolite; (I.3) drying the impregnated zeolite to obtain a catalyst precursor; and (I.4) calcining the catalyst precursor to obtain the catalyst composition.

In any embodiment, the process can further comprise: (IV) contacting the catalyst composition with a sulfur-containing agent during or after step (III) to sulfide at least a portion of the catalyst composition. Preferably step (IV) comprises: (IV.1) mixing hydrogen sulfide with the second gas to form a mixture gas comprising hydrogen sulfide at a concentration in a range of from 100 vppm to 1,000 vppm; and (IV.2) contacting the catalyst composition with the mixture gas for a period from 0.1 hour to 8 hours.

Often, the catalyst composition is for converting an aromatic hydrocarbon. Preferably the process further comprises, after step (III), and more preferably after step (IV) if present: (V) contacting the catalyst composition with one or more aromatic hydrocarbons and hydrogen under reaction conditions effective to convert the one or more aromatic hydrocarbons. For example, the catalyst composition can be a transalkylation catalyst. The one or more aromatic hydrocarbons can comprise C9+ aromatic hydrocarbons and C7-aromatic hydrocarbons. The reaction conditions often include: a weight hourly space velocity (WHSV) of the aromatic hydrocarbons from 0.2 to 100 h$^{-1}$, preferably from 2 to 5 h$^{-1}$; an absolute pressure of from 380 kPa to 3550 kPa, preferably from 1480 kPa to 3550 kPa; a molar ratio of hydrocarbons to hydrogen of from 1 to 5, preferably from 2 to 3; and a reactor inlet temperature of from 340° C. to 515° C., preferably 360° C. to 500° C. The process can produce a transalkylation product mixture comprising C8 aromatic hydrocarbons.

In any embodiment, the process can comprise the following steps in the following order: (i) providing a catalyst composition comprising a precious metal at a concentration from 0.01 wt % to 5.0 wt %, based on the total weight of the catalyst composition; (ii) disposing the catalyst composition in a reactor; (iii) purging the catalyst composition and the reactor with an inert gas; (iv) purging the catalyst composition and the reactor with a first gas comprising carbon monoxide at a concentration no greater than 0.5 vppm; (v) heating the catalyst composition from an ambient temperature to a first temperature in a range from 150° C. to 300° C.; (vi) maintaining the catalyst composition in proximity to the first temperature for a period from 1 hour to 24 hours in the presence of the first gas; (vii) heating the catalyst composition from the first temperature to a second temperature no less than 340° C.; and (viii) maintaining the catalyst composition in proximity to the second activation temperature for a period from 0.1 hour to 8 hours in the presence of a second gas comprising carbon monoxide at a concentration no less than 1 vppm.

In another aspect, the present invention provides a process for activating a catalyst composition comprising a precious metal, using an inert gas diluent. The process comprises: (1) providing the catalyst composition comprising the precious metal, wherein the concentration of the precious metal in the catalyst composition is from 0.01 wt % to 5.0 wt %, expressed as weight percentage of the precious metal based on the total weight of the catalyst composition; (2) mixing a high purity inert gas comprising no more than 1 vppm carbon monoxide, with a hydrogen gas stream comprising no more than 20 vppm carbon monoxide, to form a gas mixture comprising no less than 2 percent hydrogen by volume; and (III) contacting the catalyst composition with the gas mixture at a temperature equal to or greater than 150° C.

In any embodiment of the inert gas activation process, the high purity inert gas can comprise nitrogen. Preferably, the inert gas has a concentration of carbon monoxide no more than 0.1 vppm. Preferably the gas mixture comprises no less than 4 percent hydrogen by volume.

In any embodiment of the inert gas activation process, the hydrogen gas stream can have a carbon monoxide concentration no less than 1 vppm. Preferably the hydrogen gas stream is reformer hydrogen produced by a hydrocarbon reforming process.

In any embodiment of the inert gas activation process, the hydrogen gas stream can have a carbon monoxide concentration no more than 1 vppm. Preferably the hydrogen gas stream is electrolytic hydrogen from electrolytic decomposition of water.

In any embodiment of the inert gas activation process, the gas mixture can have a concentration of carbon monoxide more or less than 1 vppm. When the CO concentration is less than 1 vppm, the gas mixture can be used at all activation temperatures up to 515° C. When the CO concentration in the gas mixture is greater than 1 vppm, the catalyst is preferably activated at a first temperature from 150° C. to 300° C. using another hydrogen stream (or another gas mixture) with a CO concentration less than 1 vppm, and after activation at the first temperature, the gas mixture with CO concentration greater than 1 vppm can be used at a second activation temperature from 340° C. to 515° C.

With reference to the drawings in which like steps and components are identified with like numerals, FIG. 1 shows a generalized, simplified schematic process flow diagram of a transalkylation process system 100 according to embodiments of the present invention. For the purposes of simplicity and clarity, FIG. 1 does not show all of the conventional pumps, heat exchangers, lines, valves, instrumentation, control systems, etc., which are familiar to those skilled in the art. 1. In the TA process 100, aromatic hydrocarbons (CxHy) 102 are heated in heater 104 and supplied in feed line 106 to TA reactor 108. Process hydrogen 110 is combined with the aromatic hydrocarbons 102 upstream or downstream (not shown) from the heater 104 and the mixture is fed to the reactor 108 via line 106. Gas stream 112 is often recovered from the effluent 114 in separator 116, and recycled via line 118 and/or purged via line 120. The TA product is generally recovered from the separator 116 via line 122.

The process hydrogen gas 110 is often produced from a refinery (not shown) associated with the TA process 100, e.g., from a hydrocarbon reformer such as a naphtha reformer, steam methane reformer, autothermal reformer, or the like. The purity specification is typically ≥99.998 or preferably ≥99.999 volume percent hydrogen, and often contains more than 1 vppm or more than 3 vppm, up to 10 vppm or 20 vppm impurities such as carbon monoxide. Hydrogen meeting this specification is generally referred to herein as "low purity."

For the purpose of startup and catalyst activation, a high purity source of hydrogen 124 containing no more than 1 vppm carbon monoxide may be provided, preferably no more than 0.5 vppm CO, more preferably no more than 0.1 vppm CO, e.g., from electrolytic decomposition of water. An electrolytic hydrogen truck or skid unit is often available for supplying high purity hydrogen 124 typically comprising ≥99.9999 volume percent hydrogen or preferably ≥99.99999 volume percent hydrogen, and can be permanently connected to the process 100 or temporarily connected or operated for startup operations.

According to any embodiment herein, the process 100 can also comprise a source of high purity nitrogen 126, e.g., less than 1 vppm CO, preferably less than 0.5 vppm CO, more preferably less than 0.1 vppm CO. High purity nitrogen, typically separated from air and comprising ≥99.9999 volume percent nitrogen or preferably ≥99.99999 volume percent nitrogen is also sometimes available in an associated refinery, for a synthesis process, as a by-product of oxygen enrichment of air, e.g., or for instrument air, or the like. The high purity nitrogen source 126 can similarly be connected to the process 100 permanently, or temporarily connected and/or operated for startup purposes.

To enhance gas-catalyst contact during startup, the system 100 is preferably operated with recirculation of the activation gas through the system 100 of FIG. 1, e.g., via line 114, separator 116, lines 112 and 118, heater 104, line 106, and so on. The system 100 can be operated with some recirculation via line 118 and some purge via line 120 with added makeup gas, or it can be operated as a closed system or partially closed system without makeup gas and/or purge via line 120. The system 100 can also be operated on a once-through continuous basis, e.g., by purging via line 120 without recirculation.

Figure 2:
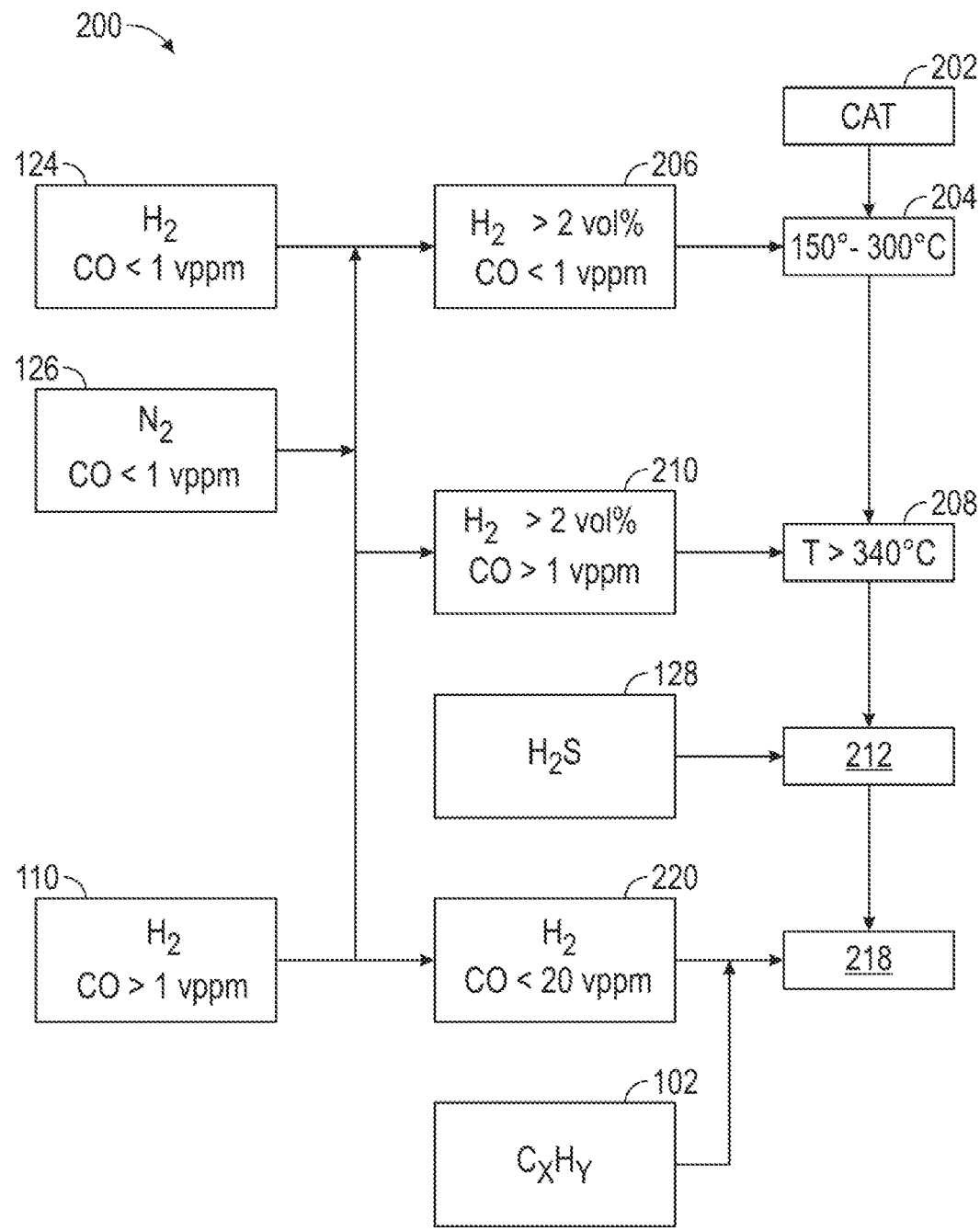
FIG. 2 is a simplified schematic showing steps for starting up the transalkylation process of FIG. 1 using hybrid activation gas and temperature profiles according to embodiments of the present invention.

FIG. 2 shows the steps for catalyst activation 200 using a hybrid temperature and activation gas profile according to embodiments of the present invention. In step 202, a catalyst having a low precious metal content, e.g., from 0.01 to 5.0 wt % precious metal, preferably 0.01 to 0.5 wt % precious metal, expressed as weight percentage of the precious metal based on the total weight of the catalyst composition, is provided. The catalyst can be a transalkylation catalyst or a different type of precious metal catalyst. TA catalyst typically comprises the precious metal on an acidic support such as zeolite, and may optionally contain a second metal function. For example, a suitable TA catalyst can comprise zeolite and the at least one precious metal, and preferably comprises at least two metals on a meso-mordenite/zeolite support, preferably wherein the two metals comprise a first metal of Group 10 of the IUPAC Periodic Table and at least one second metal of Groups 11-15 of the IUPAC Periodic Table, e.g., as described in patent document U.S. Pat. No. 10,053,403B2. The catalyst is often prepared by providing a zeolite, impregnating the zeolite with a solution of the precious metal to obtain an impregnated zeolite, drying the impregnated zeolite to obtain a catalyst precursor, and calcining the catalyst precursor to obtain the catalyst composition.

The catalyst can be loaded in the TA reactor using procedures well known to those in the art. If desired, after loading, the catalyst and reactor can be purged, e.g., with an inert gas, with a mixture of the inert gas and a hydrogen-containing gas used for activation, and/or the hydrogen-containing activating gas. Often, the catalyst composition is disposed in the reactor 108 (FIG. 1), the catalyst composition and the reactor 108 are then purged with inert gas such as high purity nitrogen 126, and next with the first gas 206. Purging generally comprises pressuring the reactor 108 and/or system 100 with the purge gas, and depressurizing the reactor 108 and/or system 100, and repeating the pressurization and depressurization a number of times, e.g., until the reactor system is free of oxygen and other impurities that may impact the catalyst.

Then, in step 204, the catalyst is contacted with a high-purity first gas containing hydrogen and no more than 1 vppm carbon monoxide, preferably no more than 0.5 vppm CO, and more preferably no more than 0.1 vppm CO, at a first temperature suitable for initial activation, e.g., 150° C. or some. The first temperature is desirably sufficiently high to achieve at least partial CO de-sensitization in the presence of the high purity first gas 206. There is no firm upper limit to the first temperature, however, any continuing use of the high-purity first gas 206 longer than necessary will reduce economic benefit. Preferably, the first temperature is between 150° C. and 300° C., more preferably 175° C. to 250° C., such as 200° C.

The first gas 206 desirably contains sufficient hydrogen for activation of the catalyst composition, preferably at least 2 volume percent hydrogen, more preferably at least 4 volume percent hydrogen. The first gas 206 can comprise or consist of high-purity hydrogen 124, e.g., electrolytic hydrogen, or it can comprise a mixture of any of the process or reformer hydrogen 110, high-purity hydrogen 124, and/or high-purity inert gas 126, which meets the needed hydrogen and CO purity requirements. For example, the first gas 206 can comprise a mixture of a high purity inert gas comprising no more than 1 vppm carbon monoxide, such as nitrogen 126, and a hydrogen gas stream comprising no more than 20 vppm carbon monoxide, such as process hydrogen 110 and/or high purity hydrogen 124, as described in more detail below in connection with FIG. 3. The first gas 206 preferably has an absolute hydrogen partial pressure in a range from 2 kPa to 5000 kPa, preferably at least 4 kPa.

The catalyst composition is often heated in the presence of the first gas from ambient temperature, which is preferably no higher than 50° C., to the first temperature, e.g., using the heater 104 (FIG. 1) to heat the feed to the reactor 108. The heating should be sufficiently slow to avoid hot spots and metal sintering, whereas a heating rate that is too slow has less economic benefit. In any embodiment, the temperature elevation rate can be in a range from 0.01° C. per minute to 5° C. per minute. Preferably, the temperature elevation rate is no more than 1° C. per minute, e.g., 0.5° C. per minute to 1° C. per minute.

During the contact step 204, the precious metal is reduced by binding with the hydrogen from the first gas. The hydrogen can be replaced in the system 100 (FIG. 1) by adding makeup gas or using a once-through operating mode, or where the system 100 is closed, the hydrogen concentration in the first gas can be allowed to decline as the hydrogen binds with the precious metal. The catalyst composition is preferably maintained in contact with first gas at the first temperature for a period of time sufficient to substantially reduce the sensitivity of the catalyst composition to carbon monoxide. Preferably, the catalyst composition is held in proximity to the first temperature in the presence of the first gas for a period of from 1 hour to 24 hours, more preferably from 3 hours to 12 hours.

In the next step 208, the catalyst composition is contacted with a second gas 210 at a second temperature not lower than 340° C. Lower temperatures may not achieve complete activation, whereas excessively high temperature can result in metal sintering or otherwise adversely impact catalyst performance Preferably, the second temperature is no higher than 515° C., more preferably no higher than 425° C. The second gas 210 likewise contains sufficient hydrogen for activation of the catalyst composition, as with the first gas 206, e.g., preferably at least 2 volume percent hydrogen, more preferably at least 4 volume percent hydrogen. The second gas 210 may contain high purity nitrogen 126 and/or high purity hydrogen 124, however, at this point the catalyst composition has already been de-sensitized to carbon monoxide and the second gas 210 preferably comprises a higher CO content than the first gas 206. Often, the second gas 210 consists primarily of hydrogen (>50 volume percent) or consists essentially of hydrogen, e.g., it can be no less than 99.998 volume percent hydrogen such as the process hydrogen gas 110 used in post-startup operations for transalkylation of the aromatic hydrocarbons 102. The second gas 210 preferably has an absolute hydrogen partial pressure in a range from 2 kPa to 5000 kPa, preferably at least 4 kPa.

In step 208, the high purity of the activation gas is not as critical since the catalyst composition may already be at least partially de-sensitized to the presence of carbon monoxide. Thus, to reduce the amount of high purity hydrogen or inert gas for the catalyst composition activation, the second gas 210 can and preferably does comprise a carbon monoxide concentration greater than 1 vppm, e.g., from 3 to 20 vppm CO, such as reformer hydrogen produced by a hydrocarbon reforming process, preferably where the CO concentration is no greater than 10 vppm.

The catalyst composition is often heated from the first temperature to the second temperature, e.g., using the heater 104 (FIG. 1) to heat the feed to the reactor 108, in the presence of the first gas 206, the second gas 210, or a mixture of both. For example, before or during the heating, the first gas 206 present in the system 100 following step 204 can be purged via line 120 by depressurizing the system 100, and then the system 100 can be pressurized with the second gas 210; and/or the first gas 206 can recirculated via line 118 as the second gas 210 is added as a makeup and/or to pressurize the system 100. In any embodiment, the temperature elevation rate can be in a range from 0.01° C. per minute to 5° C. per minute. Preferably, the temperature elevation rate is no more than 1° C. per minute, e.g., 0.5° C. per minute to 1° C. per minute.

During the contact step 208, the catalyst composition is further activated. The system 100 (FIG. 1) can be operated in catalyst activation mode by adding makeup gas or using a once-through operating mode, or the system 100 can be closed, preferably with recirculation via line 118. The catalyst composition is preferably maintained in contact with second gas 210 at the second temperature for a period of time sufficient to substantially complete activation of the catalyst composition. Preferably, the catalyst composition is held in proximity to the second temperature in the presence of the second gas for a period of from 0.2 hour to 8 hours, more preferably from 0.5 hour to 4 hours.

In step 212, the catalyst composition can optionally be contacted with a sulfur-containing agent 214 such as hydrogen sulfide, during or after step 212, to sulfide at least a portion of the catalyst composition. Step 212 preferably comprises mixing hydrogen sulfide with the process hydrogen 110, and/or second gas 210 if different, to form a mixture gas comprising hydrogen sulfide, often at a concentration in a range of from 100 vppm to 1000 vppm, and contacting the catalyst composition with the mixture gas for a period from 0.1 hour to 8 hours.

After catalyst activation, the reactor 108 can be operated in a production mode in step 218. Where the reactor 108 is used for transalkylation, after step 208 and/or preferably after step 212 if present, step 218 can comprise contacting the catalyst composition with a feed 220 comprising one or more aromatic hydrocarbons and hydrogen under reaction conditions effective to convert the one or more aromatic hydrocarbons to transalkylation products. For example, the catalyst composition can be a transalkylation catalyst. The one or more aromatic hydrocarbons can comprise C9+ aromatic hydrocarbons such as trimethyl benzenes and C7-aromatic hydrocarbons such as toluene and/or benzene, and the transalkylation products can comprise C8 aromatic hydrocarbons such as paraxylenes. Transalkylation conditions often include: a weight hourly space velocity (WHSV) of the aromatic hydrocarbons from 0.2 to 100 h$^{-1}$, preferably from 2 to 5 h$^{-1}$; an absolute pressure of from 380 kPa to 3550 kPa, preferably from 1480 kPa to 3550 kPa; a molar ratio of hydrocarbons to hydrogen of from 1 to 5, preferably from 2 to 3; and a reactor inlet temperature of from 340° C. to 515° C., preferably 360° C. to 500° C.

Figure 3:
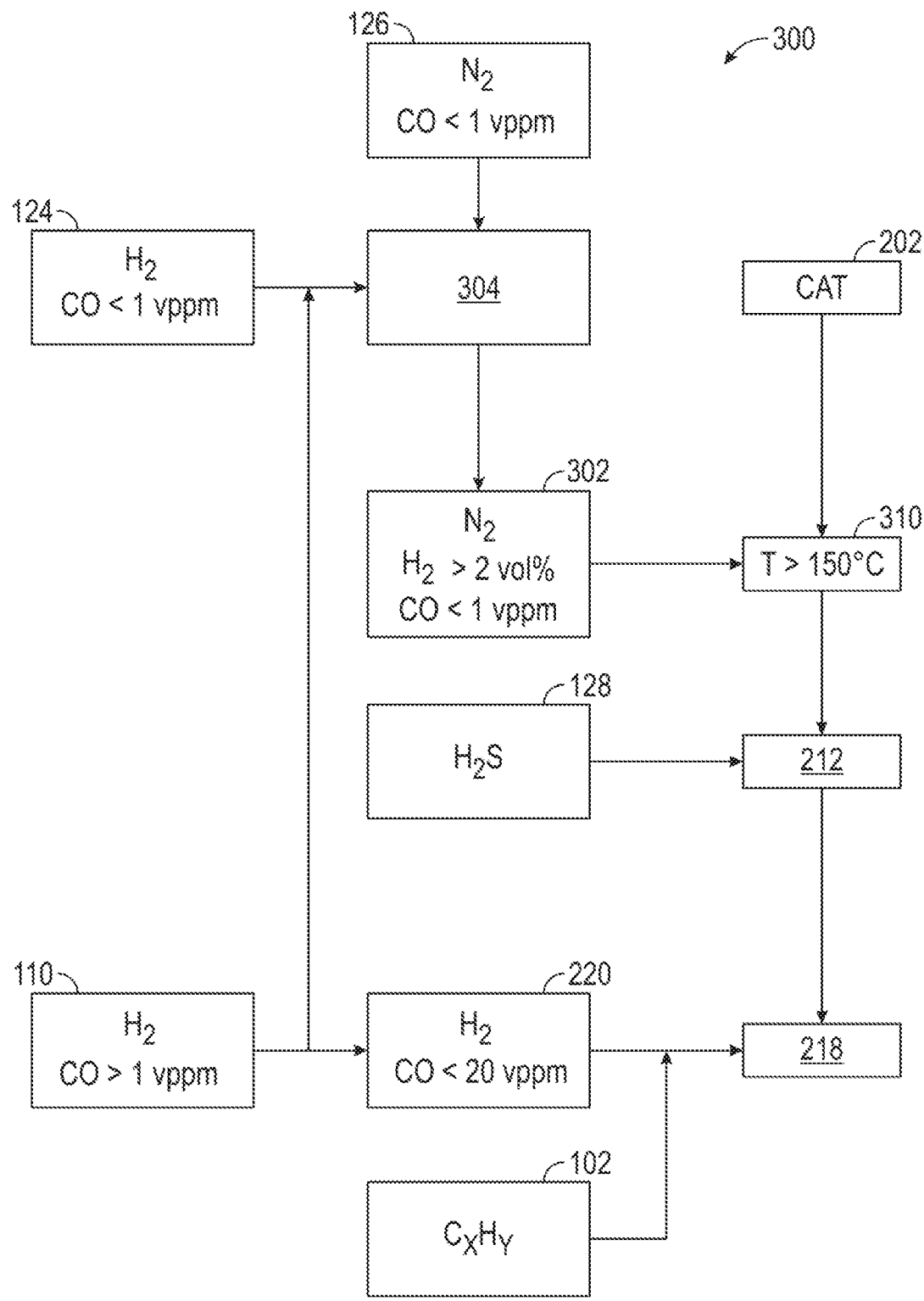
FIG. 3 is a simplified schematic showing steps for starting up the transalkylation process of FIG. 1 using a gas mixture of hydrogen and nitrogen in the activation gas according to embodiments of the present invention.

FIG. 3 shows the steps for activation 300 of a catalyst composition comprising a precious metal using a gas mixture 302 comprising high purity nitrogen 126 and hydrogen 110 or 124 according to embodiments of the present invention. In step 202, a catalyst composition comprising the precious metal is provided as described above in connection with FIG. 2.

The gas mixture 302 is prepared in step 304 by combining high purity nitrogen 126 and hydrogen 110 or 124, e.g., by introducing them together into a line such as line 106 (FIG. 1) before contact with the catalyst composition in the reactor 108. In step 304, a high purity inert gas 126 comprising no more than 1 vppm carbon monoxide, preferably no more than 0.5 vppm CO, more preferably no more than 0.1 vppm, is mixed with hydrogen 110 or 124 comprising no more than 20 vppm carbon monoxide, preferably no more than 10 vppm CO, to form the gas mixture 302 comprising no less than 2 percent hydrogen by volume, preferably no less than 4 percent hydrogen by volume.

In step 310, the catalyst composition is contacted with the gas mixture 302 from step 304 at a temperature no lower than 150° C., e.g., 150° C. to 515° C. For example, the catalyst composition can be activated by contact with the gas mixture from step 304 to an ultimate activation temperature no less than 340° C., e.g., 340° C. to 515° C., preferably 360° C. to 500° C.

Or, activation of the catalyst composition in step 310 can be completed in a hybridized manner as in FIG. 2, e.g., using the gas mixture 302 from step 304 as the first gas 206 at the first temperature to at least partially de-sensitize the catalyst composition to carbon monoxide, and then using the low purity second gas 210 (1 vppm<CO<20 vppm) at the higher second temperature. For example, the first temperature can be no lower than 150° C., e.g., 150° C. to 300° C., and the second temperature can be higher than the first temperature, e.g., no less than 340° C., preferably 340° C. to 515° C., more preferably 360° C. to 500° C. The low purity second gas 210 preferably comprises no less than 1 vppm CO, more preferably no less than 3 vppm CO, e.g., 3-10 vppm CO. The low purity second gas 210 preferably comprises, consists essentially of, or consists of process hydrogen 110.

As described above in connection with FIG. 2, the activation process 300 can also optionally include sulfiding in step 212 with hydrogen sulfide gas 128, using gas 302 and/or process hydrogen 110, and then operation step 218 proceeds using gas 220 and aromatic hydrocarbons 102.

ADDITIONAL EMBODIMENTS

This disclosure may include one or more of the following additional embodiments:

Embodiment 1. 1. A process for activating a catalyst composition comprising a precious metal, the process comprising:
(I) providing the catalyst composition comprising the precious metal, wherein the concentration of the precious metal in the catalyst composition is from 0.01 wt % to 5.0 wt %, expressed as weight percentage of the precious metal based on the total weight of the catalyst composition;
(II) contacting the catalyst composition with a first gas at a first temperature in a range from 150° C. to 300° C., the first gas comprising hydrogen and no more than 1 vppm carbon monoxide; and
(III) after step (II), contacting the catalyst composition with a second gas at a second temperature not lower than 340° C., wherein the second gas comprises hydrogen and carbon monoxide at a concentration no less than 1 vppm.

Embodiment 2. The process of Embodiment 1, wherein the first gas further comprises an inert gas, preferably nitrogen.

Embodiment 3. The process of Embodiment 1, wherein the second gas comprises hydrogen and a concentration of carbon monoxide no less than 3 vppm and no greater than 20 vppm, preferably wherein the second gas comprises reformer hydrogen produced by a hydrocarbon reforming process and the carbon monoxide concentration is no greater than 10 vppm.

Embodiment 4. The process of Embodiment 3, wherein the first gas is formed by diluting the reformer hydrogen with high purity inert gas to decrease the carbon monoxide concentration of the resulting first gas relative to the reformer hydrogen, preferably wherein the inert gas comprises carbon monoxide at a concentration of no more than 0.1 vppm.

Embodiment 5. The process of Embodiment 1, wherein the first gas comprises at least 2 volume percent hydrogen and no more than 98 volume percent inert gas, preferably at least 4 volume percent hydrogen and no more than 96 volume percent inert gas.

Embodiment 6. The process of Embodiment 1, wherein the first gas comprises carbon monoxide at a concentration of no greater than 0.5 vppm, preferably no greater than 0.1 vppm.

Embodiment 7. The process of Embodiment 1, wherein the first gas comprises or consists of an electrolytic hydrogen stream formed by electrolytic decomposition of water.

Embodiment 8. The process of any of the preceding Embodiments, wherein the catalyst composition comprises the precious metal at a concentration no greater than 0.1 wt %, based on the total weight of the catalyst composition.

Embodiment 9. The process of Embodiment 1, the process further comprising, after step (I) and before step (II): (Ia) heating the catalyst composition in the presence of the first gas from ambient temperature to the first temperature, preferably wherein the ambient temperature is no higher than 50° C.

Embodiment 10. The process of Embodiment 1, wherein the process further comprises, after step (II) and before step (III): (IIa) heating the catalyst composition from the first temperature to the second temperature in the presence of the first gas, the second gas, or a mixture of both.

Embodiment 11. The process of Embodiment 9 wherein the heating in respective steps (Ia) and (IIa) comprises heating the catalyst composition at a temperature elevation rate in a range from 0.01° C. per minute to 5° C. per minute, preferably the temperature elevation rate is no more than 1° C. per minute.

Embodiment 12. The process of Embodiment 1, wherein the process further comprises:
(I-A) after step (I) and before step (II), disposing the catalyst composition in a reactor;
(I-B) after step (I-A), purging the catalyst composition and the reactor with inert gas; and
(I-C) after step (I-B), purging the catalyst composition and the reactor with the first gas.

Embodiment 13. The process of Embodiment 1, further comprising: wherein in step (II), the catalyst composition is held in proximity to the first temperature in the presence of the first gas for a period of from 1 hour to 24 hours, preferably from 3 hours to 12 hours; and/or wherein in step (III), the catalyst composition is held in proximity to the second temperature in the presence of the second gas for a period of from 0.2 hour to 8 hours, preferably from 0.5 hour to 4 hours.

Embodiment 14. The process of Embodiment 1, further comprising:
wherein the second temperature is no higher than 515° C., preferably no higher than 425° C.; and/or
wherein first and second gases have an absolute hydrogen partial pressure in a range from 2 kPa to 5000 kPa, preferably at least 4 kPa.

Embodiment 15. The process of Embodiment 1, wherein step (I) comprises:
(L1) providing a zeolite;
(L2) impregnating the zeolite with a solution of the precious metal to obtain an impregnated zeolite;
(L3) drying the impregnated zeolite to obtain a catalyst precursor; and
(L4) calcining the catalyst precursor to obtain the catalyst composition.

Embodiment 16. The process of Embodiment 1, the process further comprising:
(IV) contacting the catalyst composition with a sulfur-containing agent during or after step (III) to sulfide at least a portion of the catalyst composition, preferably wherein step (IV) comprises:
(IV.1) mixing hydrogen sulfide with the second gas to form a mixture gas comprising hydrogen sulfide at a concentration in a range of from 100 vppm to 1,000 vppm; and
(IV.2) contacting the catalyst composition with the mixture gas for a period from 0.1 hour to 8 hours.

Embodiment 17. The process of Embodiment 1, wherein the catalyst composition is for converting an aromatic hydrocarbon, preferably wherein the process further comprises, after step (III), and more preferably after step (IV) if present: (V) contacting the catalyst composition with one or more aromatic hydrocarbons and hydrogen under reaction conditions effective to convert the one or more aromatic hydrocarbons.

Embodiment 18. The process of Embodiment 17, wherein:
is the catalyst composition is a transalkylation catalyst;
the one or more aromatic hydrocarbons comprise C9+ aromatic hydrocarbons and C7-aromatic hydrocarbons;
the reaction conditions include:
a weight hourly space velocity (WHSV) of the aromatic hydrocarbons from 0.2 to 100 $h^{-1}$, preferably from 2 to 5 $h^{-1}$;
an absolute pressure of from 380 kPa to 3550 kPa, preferably from 1480 kPa to 3550 kPa;
a molar ratio of hydrocarbons to hydrogen of from 1 to 5, preferably from 2 to 3; and
a reactor inlet temperature of from 340° C. to 515° C., preferably 360° C. to 500° C.; and
the process produces a transalkylation product mixture comprising C8 aromatic hydrocarbons.

Embodiment 19. A process for activating a catalyst composition, the process comprising the following steps in the following order:
(i) providing a catalyst composition comprising a precious metal at a concentration from 0.01 wt % to 5.0 wt %, based on the total weight of the catalyst composition;
(ii) disposing the catalyst composition in a reactor;
(iii) purging the catalyst composition and the reactor with an inert gas;
(iv) purging the catalyst composition and the reactor with a first gas comprising carbon monoxide at a concentration no greater than 0.5 vppm;
(v) heating the catalyst composition from an ambient temperature to a first temperature in a range from 150° C. to 300° C.;
(vi) maintaining the catalyst composition in proximity to the first temperature for a period from 1 hour to 24 hours in the presence of the first gas;
(vii) heating the catalyst composition from the first temperature to a second temperature no less than 340° C.; and
(viii) maintaining the catalyst composition in proximity to the second activation temperature for a period from 0.1 hour to 8 hours in the presence of a second gas comprising carbon monoxide at a concentration no less than 1 vppm.

Embodiment 20. A process for activating a catalyst composition comprising a precious metal, the process comprising:
- (I) providing the catalyst composition comprising the precious metal, wherein the concentration of the precious metal in the catalyst composition is from 0.01 wt % to 5.0 wt %, expressed as weight percentage of the precious metal based on the total weight of the catalyst composition;
- (II) mixing a high purity inert gas comprising no more than 1 vppm carbon monoxide, with a hydrogen gas stream comprising no more than 20 vppm carbon monoxide, to form a gas mixture comprising no less than 2 percent hydrogen by volume; and
- (III) contacting the catalyst composition with the gas mixture at a temperature no lower than 150° C.

Embodiment 21. The process of Embodiment 20, wherein the high purity inert gas comprises nitrogen and has a concentration of carbon monoxide no more than 0.1 vppm, preferably wherein the gas mixture comprises no less than 4 percent hydrogen by volume.

Embodiment 22. The process of Embodiment 20, wherein the hydrogen gas stream has a carbon monoxide concentration no less than 1 vppm, preferably wherein the hydrogen gas stream is reformer hydrogen produced by a hydrocarbon reforming process.

Embodiment 23. The process of any of Embodiment 20, wherein the hydrogen gas stream has a carbon monoxide concentration no more than 1 vppm, preferably wherein the hydrogen gas stream is electrolytic hydrogen from the electrolytic decomposition of water.

Embodiment 24. The process of Embodiment 20, wherein the gas mixture has a concentration of carbon monoxide no more than 1 vppm, preferably no more than 0.5 vppm.

Embodiment 25. The process of Embodiment 20, wherein the gas mixture has a concentration of carbon monoxide no less than 1 vppm, and wherein the temperature in step (III) is greater than or equal to 340° C.

EXAMPLES

In the following examples, a transalkylation (TA) catalyst containing 0.03 wt % Pt ("Catalyst A") was evaluated in an adiabatic pilot plant TA reactor service. A typical TA feed comprising a mixture of 50 wt % heavy aromatic reformate (HAR) from a refinery and 50 wt % toluene was used. Whole extrudates of Catalyst A were mixed with an equal weight of inert diluent and loaded in the reactor. Performance was evaluated under the conditions in Table A:

TABLE A

| TA operating conditions | |
|---|---|
| WHSV, h$^{-1}$ | 3 |
| Pressure, MPa (psig) | 2.48 (360) |
| Hydrogen:hydrocarbon ratio, molar | 2.0 |
| Reactor inlet temperature, ° C. (° F.) | 349 (660) |
| Catalyst A, gram | 30 |

Comparative 1: Baseline performance with electrolytic hydrogen activation. The pilot plant was started up with electrolytic hydrogen (CO<0.1 vppm) for activation and then switched to reformer-sourced hydrogen (10 vppm CO) using the procedure in Table B-1. The activation procedure was repeated if different TA reactor temperatures were to be evaluated.

TABLE B-1

| Start procedure for one activation gas (0.1-10 vppm CO in H$_2$) | |
|---|---|
| Step 1 | Pressurize unit to 2.48 MPa (360 psig) with activation gas (0.1-10 vppm CO/H$_2$) |
| Step 2 | Initiate flow of activation gas through the unit at 37.7 L/h (1.33 SCFH) and ambient temperature (21° C. (70° F.)) for 3 h |
| Step 3 | Increase reactor temperature to 346° C. (655° F.) at 33.3° C./h (60° F./h) |
| Step 4 | Maintain conditions for 2 h at 346° C. (655° F.) |
| Step 5 | Sulfide with 400 vppm H$_2$S in activation gas for 60 min at 37.7 L/h (1.33 SCFH) |
| Step 7 | Initiate HAR*/toluene feed and maintain sulfiding gas flow for 1 h |
| Step 8 | Switch to source H$_2$ (0.1 vppm CO/H$_2$) |

*Heavy aromatic hydrocarbon

Transalkylation of toluene and C9+ aromatics to mixed xylenes generally involves catalysts with an acid function, often from zeolite, and a metal function from one or more metals. As shown schematically in FIG. 2, in the main reactions, toluene and C9+ aromatics are transalkylated to form xylenes. However, de-alkylation and naphthene cracking also occur to produce light olefins, which must be rapidly removed to avoid forming coke and/or re-alkylating aromatics. The metal function promotes the saturation of alkenes to inert paraffins. Sintering of the metal function by CO decreases efficiency of hydrogenation reactions thus increasing concentration of EB and other ethylated species. Increasing the transalkylation temperature when the metal function has been sintered can often recover some of the lost efficiency, but leads to an undesirably shortened run length for the cycle. Increasing the TA temperature of a catalyst properly activated without sintering otherwise leads to hyperactivity and undesirable destruction of the aromatic molecules.

In these examples, de-ethylation was used as a measure of methyl and ethyl removal from C9+ aromatics, such as methyl, ethyl-benzene and diethylbenzene. The ratio of ethane to ethylene was used as a measure of hydrogenation efficiency, and the degree of suppression of ethylbenzene (EB) generation was measured by ethylbenzene yield. For this catalyst at the described process conditions, the specifications were de-ethylation >90 wt % and ethylbenzene yield <0.3 wt %. The ethane/ethene weight ratio should be very high, e.g., >2000.

After metal reduction using electrolytic hydrogen (CO<0.1 vppm), operating the TA reactor at a temperature of 377° C. (711° F.) resulted in a de-ethylation rate of 94 wt % and an ethylbenzene yield of 0.18 wt %. The weight ratio of ethane to ethene in the effluent was ~3800.

Comparative 2: Upper baseline performance with reformer (source) hydrogen activation. The pilot plant was started up with reformer hydrogen (10 vppm CO) for activation using the procedure in Table B-1. After metal reduction, operating the TA reactor at a temperature of 370° C. (698° F.) resulted in a de-ethylation rate of 58 wt %, an ethylbenzene yield of 1.50 wt %, and an ethane/ethene ratio of ~200. After repeating the activation procedures with fresh catalyst, increasing the TA operating temperature to 380° C. (716° F.) increased the de-ethylation rate to 77 wt %, increased the ethane/ethene ratio to ~380, and reduced the ethylbenzene yield to 0.73 wt %. Further increasing the TA operating temperature to 406° C. (763° F.) only increased the de-ethylation rate to 88 wt %, ethane/ethene ratio to ~470, and reduced ethylbenzene yield to 0.46 wt %. In contrast, base catalyst activated with high purity hydrogen (CO<0.1 vppm) typically becomes hyperactive (de-ethylation rate 100%) at elevated temperatures.

Example 1: Hybrid activation with first (electrolytic) and second (reformer hydrogen) activation gases. The pilot plant was started up with electrolytic hydrogen (CO<0.1 vppm) for activation to 200° C. and then switched to reformer-sourced hydrogen (10 vppm CO) to complete the activation. The two-activation gas procedure is set out in Table B-2. After metal reduction, operating the TA reactor at a temperature of 377° C. (711° F.) resulted in a de-ethylation rate of 88 wt %, an ethylbenzene yield of 0.39 wt %, and an ethane/ethene ratio of ~3600.

The data for Example 1 are presented in Table 1 with the data for Comparatives 1 and 2. Example 1 demonstrates that activation with a hybrid procedure using high purity hydrogen (e.g., 0.1 vppm CO) to a relatively low first activation temperature, followed by activation with low purity hydrogen (e.g., 10 vppm CO) to an ultimate second activation temperature, can obtain a TA reactor performance approaching that of using the high purity hydrogen during the entire hydrogen activation procedure.

TABLE B-2

Hybrid start procedure for two activation gases (0.1-10 vppm CO in $H_2$)

| Step | Description |
|---|---|
| Step 1 | Pressurize unit to 2.48 MPa (360 psig) with first activation gas (0.1-10 vppm CO/$H_2$) |
| Step 2 | Initiate flow of activation gas through the unit at 37.7 L/h (1.33 SCFH) and ambient temperature (21° C. (70° F.)) for 3 h |
| Step 3a | Increase reactor temperature to 200° C. (392° F.) at 33.3° C./h (60° F./h) |
| Step 3b | Maintain conditions at 200° C. (392° F.) for 8 h |
| Step 3c | Switch to second activation gas (10 vppm CO/$H_2$) |
| Step 3d | Increase reactor temperature to 346° C. (655° F.) at 33.3° C./h (60° F./h) |
| Step 4 | Maintain conditions for 2 h at 346° C. (655° F.) |
| Step 5 | Sulfide with 400 vppm $H_2S$ in second activation gas for 60 min at 37.7 L/h (1.33 SCFH) |
| Step 6 | Initiate HAR*/toluene feed and maintain sulfiding gas flow for 1 h |
| Step 7 | Switch back to source $H_2$ (<0.1 vppm CO/$H_2$) |

*Heavy aromatic hydrocarbon

TABLE 1

TA reactor operating performance with/without hybrid activation

| Catalyst system | Comparative 1 | Comparative 2 | | | Example 1 |
|---|---|---|---|---|---|
| | A | A | A | A | A |
| Activation process | | | | | |
| $1^{st}$ Activation Gas CO in H2 during activation to 200° C. (vppm) | <1 | 10 | 10 | 10 | <1 |
| $2^{nd}$ Activation Gas CO in H2 during activation to 346° C. (655° F.) (vppm) | <1 | 10 | 10 | 10 | 10 |
| Transalkylation reactor operating conditions | | | | | |
| C9+ (wt %) | 50 | 50 | 50 | 50 | 50 |
| Toluene (wt %) | 50 | 50 | 50 | 50 | 50 |
| Pressure (MPa (psig)) | 2.48 (360) | 2.48 (360) | 2.48 (360) | 2.48 (360) | 2.48 (360) |
| WHSV ($h^{-1}$) | 3 | 3 | 3 | 3 | 3 |
| Reactor Temperature (° C.) | 377 | 370 | 389 | 406 | 377 |
| H2:HC molar ratio | 2 | 2 | 2 | 2 | 2 |
| Reactor performance | | | | | |
| Ethane/Ethene Ratio | ~3800 | ~200 | ~380 | ~470 | ~3600 |
| Ethylbenzene Yield (wt %) | 0.18 | 1.50 | 0.73 | 0.46 | 0.39 |
| Ethyl Aromatics Conversion (wt %) | 94 | 58 | 77 | 86 | 88 |

Example 2. Hybrid activation using N2-diluted reformer hydrogen to <1 vppm CO. In these examples the catalyst was activated using the hybrid procedure of Table B-2 and the TA operating conditions of Table A except the reactor temperature was 377° C. The low purity hydrogen (10 vppm CO) was diluted with high purity nitrogen (<0.1 vppm CO) at a volume ratio of 10% hydrogen and 90% nitrogen. The resulting first activation gas contained 10 volume percent hydrogen and 1 vppm CO. TA reactor performance showed a de-ethylation rate of 92%.

Comparatives 3 and 4. Hybrid activation using N2-diluted reformer hydrogen to >1 vppm CO. In comparative examples 3 and 4 the low purity hydrogen (10 vppm CO) was diluted less, resulting in the first activation gas containing 2 or 3 vppm CO, using only 80 or 70 volume percent nitrogen, respectively. At these higher CO levels the de-ethylation dropped below 80 percent. The data are presented in Table 2 with that of Example 1 and Comparatives 1 and 2.

TABLE 2

Catalyst activation using reformer hydrogen diluted with high purity nitrogen

| Run | Comparative 1 | Comparative 2 | Example 2 | Comparative 3 | Comparative 4 |
|---|---|---|---|---|---|
| Reformer H2 (10 vppm CO) | 0 | 100 | 10% | 20% | 30% |
| Electrolytic H2 (CO < 0.1 vppm) | 100 | 0 | 0 | 0 | 0 |
| N2 (CO < 0.1 vppm) | 0 | 0 | 90% | 80% | 70% |
| Total CO, vppm | 0.1 | 10 | 1 | 2 | 3 |
| De-ethylation, % | 94 | 58 | 92 | 77 | 79 |

Example 2 demonstrates that TA catalyst can be successfully activated with high purity nitrogen dilution of low purity hydrogen as the first activation gas in the hybrid activation process, without any high purity hydrogen. A similar result is obtained by highly diluting high purity hydrogen with the nitrogen, provided the first activation gas has a hydrogen proportion sufficient for catalyst activation, e.g., starting with at least 2 or 4 volume percent hydrogen. The amount of high purity hydrogen required for the hybrid activation process is thus substantially reduced or eliminated.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

What is claimed is:

1. A process for activating a catalyst composition comprising a precious metal, the process comprising:
   (I) providing the catalyst composition comprising the precious metal, wherein the concentration of the precious metal in the catalyst composition is from 0.01 wt % to 5.0 wt %, expressed as weight percentage of the precious metal based on the total weight of the catalyst composition;
   (II) contacting the catalyst composition with a first gas at a first temperature in a range from 150° C. to 300° C., the first gas comprising hydrogen and no more than 1 vppm carbon monoxide, based on the total volume of the first gas; and
   (III) after step (II), contacting the catalyst composition with a second gas comprising hydrogen at a second temperature not lower than 340° C., wherein the second gas further comprises carbon monoxide at a concentration of no less than 1 vppm, based on the total volume of the second gas.

2. The process of claim 1, wherein the first gas further comprises an inert gas.

3. The process of claim 2, wherein the first gas is formed by diluting a reformer hydrogen with a high purity inert gas to decrease the carbon monoxide concentration of the resulting first gas relative to the reformer hydrogen.

4. The process of claim 1, wherein the second gas comprises carbon monoxide at a concentration of no less than 3 vppm and no greater than 20 vppm, based on the total volume of the second gas.

5. The process of claim 1, wherein the first gas comprises at least 2 volume percent hydrogen and no more than 98 volume percent inert gas.

6. The process of claim 1, wherein the first gas comprises carbon monoxide at a concentration of no greater than 0.5 vppm.

7. The process of claim 1, wherein the first gas comprises an electrolytic hydrogen stream formed by electrolytic decomposition of water.

8. The process of claim 1, wherein the catalyst composition comprises the precious metal at a concentration no greater than 0.1 wt %, based on the total weight of the catalyst composition.

9. The process of claim 1, the process further comprising, after step (I) and before step (II):
   (Ia) heating the catalyst composition in the presence of the first gas from ambient temperature to the first temperature.

10. The process of claim 9, wherein the heating in respective steps (Ia) and (IIa) comprises heating the catalyst composition at a temperature elevation rate in a range from 0.01° C. per minute to 5° C. per minute.

11. The process of claim 1, wherein the process further comprises, after step (II) and before step (III):
    (IIa) heating the catalyst composition from the first temperature to the second temperature in the presence of the first gas, the second gas, or a mixture of both.

12. The process of claim 1, wherein the process further comprises:
    (I-A) after step (I) and before step (II), disposing the catalyst composition in a reactor;
    (I-B) after step (I-A), purging the catalyst composition and the reactor with an inert gas; and
    (I-C) after step (I-B), purging the catalyst composition and the reactor with the first gas.

13. The process of claim 1, further comprising:
    wherein in step (II), the catalyst composition is held in proximity to the first temperature in the presence of the first gas for a period of from 1 hour to 24 hours; and/or wherein in step (III), the catalyst composition is held in proximity to the second temperature in the presence of the second gas for a period of from 0.2 hour to 8 hours.

14. The process of claim 1, further comprising:
    wherein the second temperature is no higher than 515° C.; and/or
    wherein first and second gases have an absolute hydrogen partial pressure in a range from 2 kPa to 5000 kPa.

15. The process of claim 1, wherein step (I) comprises:
    (I.1) providing a zeolite;
    (I.2) impregnating the zeolite with a solution of the precious metal to obtain an impregnated zeolite;
    (I.3) drying the impregnated zeolite to obtain a catalyst precursor; and
    (I.4) calcining the catalyst precursor to obtain the catalyst composition.

16. The process of claim 1, the process further comprising:
    (IV) contacting the catalyst composition with a sulfur-containing agent during or after step (III) to sulfide at least a portion of the catalyst composition.

17. The process of claim 1, wherein the catalyst composition is for converting an aromatic hydrocarbon, wherein the process further comprises, after step (III):
  (V) contacting the catalyst composition with one or more aromatic hydrocarbons and hydrogen under reaction conditions effective to convert the one or more aromatic hydrocarbons.

18. The process of claim 17, wherein:
  the catalyst composition is a transalkylation catalyst;
  the one or more aromatic hydrocarbons comprise C9+ aromatic hydrocarbons and C7− aromatic hydrocarbons;
  the reaction conditions include:
    a weight hourly space velocity (WHSV) of the aromatic hydrocarbons from 0.2 to 100 $h^{-1}$;
    an absolute pressure of from 380 kPa to 3550 kPa;
    a molar ratio of hydrocarbons to hydrogen of from 1 to 5; and
    a reactor inlet temperature of from 340° C. to 515° C.; and
  the process produces a transalkylation product mixture comprising C8 aromatic hydrocarbons.

19. A process for activating a catalyst composition, the process comprising the following steps in the following order:
  (i) providing a catalyst composition comprising a precious metal at a concentration from 0.01 wt % to 5.0 wt %, based on the total weight of the catalyst composition;
  (ii) disposing the catalyst composition in a reactor;
  (iii) purging the catalyst composition and the reactor with an inert gas;
  (iv) purging the catalyst composition and the reactor with a first gas comprising carbon monoxide at a concentration no greater than 0.5 vppm;
  (v) heating the catalyst composition from an ambient temperature to a first temperature in a range from 150° C. to 300° C.;
  (vi) maintaining the catalyst composition in proximity to the first temperature for a period from 1 hour to 24 hours in the presence of the first gas;
  (vii) heating the catalyst composition from the first temperature to a second temperature no less than 340° C.; and
  (viii) maintaining the catalyst composition in proximity to the second activation temperature for a period from 0.1 hour to 8 hours in the presence of a second gas comprising carbon monoxide at a concentration no less than 1 vppm.

20. A process for activating a catalyst composition comprising a precious metal, the process comprising:
  (I) providing the catalyst composition comprising the precious metal, wherein the concentration of the precious metal in the catalyst composition is from 0.01 wt % to 5.0 wt %, expressed as weight percentage of the precious metal based on the total weight of the catalyst composition;
  (II) mixing a high purity inert gas comprising no more than 1 vppm carbon monoxide, with a hydrogen gas stream comprising no less than 1 vppm and no more than 20 vppm carbon monoxide, to form a gas mixture comprising no less than 2 percent hydrogen by volume; and
  (III) contacting the catalyst composition with the gas mixture at a temperature no lower than 150° C.

21. The process of claim 20, wherein the high purity inert gas comprises nitrogen and has a concentration of carbon monoxide no more than 0.1 vppm.

22. The process of claim 20, further comprising, before step (II), producing the hydrogen gas stream by a hydrocarbon reforming process.

23. The process of claim 20, wherein the gas mixture has a concentration of carbon monoxide no more than 1 vppm.

24. The process of claim 20, wherein the temperature in step (III) is greater than or equal to 340° C.

\* \* \* \* \*